United States Patent
Gilchrist et al.

[11] Patent Number: 5,972,371
[45] Date of Patent: Oct. 26, 1999

[54] BIODEGRADABLE DEVICE

[75] Inventors: Thomas Gilchrist; David Michael Healy, both of Ayr, United Kingdom

[73] Assignee: Giltech Limited, Ayr, United Kingdom

[21] Appl. No.: 08/930,221

[22] PCT Filed: Apr. 1, 1996

[86] PCT No.: PCT/GB96/00784

§ 371 Date: Sep. 30, 1997

§ 102(e) Date: Sep. 30, 1997

[87] PCT Pub. No.: WO96/31160

PCT Pub. Date: Oct. 10, 1996

[30]     Foreign Application Priority Data

Apr. 1, 1995 [GB] United Kingdom .................. 9506796

[51] Int. Cl.⁶ ........................................................ A61F 2/06
[52] U.S. Cl. ........................................... 424/426; 523/115
[58] Field of Search .............................. 424/426; 523/115

[56]             References Cited

U.S. PATENT DOCUMENTS 3,786,817  1/1974  Palma .
4,863,668  9/1989  Griffiths et al. .
4,963,146  10/1990 Li .

FOREIGN PATENT DOCUMENTS

| 0226061 | 6/1987 | European Pat. Off. . |
| 3227984 | 2/1984 | Germany . |
| 2099702 | 12/1982 | United Kingdom . |
| 88/06866 | 9/1988 | WIPO . |
| 90/08470 | 8/1990 | WIPO . |

*Primary Examiner*—Carlos Azpuru
*Attorney, Agent, or Firm*—Ratner & Prestia

[57]             ABSTRACT

There is provided a device to promote healing of cut tissue members, such as nerves, tendon or muscles, within a body. The device is of hollow construction and comprises apertures into which the cut ends of the tissue members are placed and fixed, usually by a fibrin-based tissue glue. Located between the apertures is a substance to promote healing of the tissue member such as, for example, nerve growth factor. Optionally the device may be used in conjunction with the external reservoir of the substance and/or with a time-operated pump to deliver the substance to the device. The device is biodegradable and is preferably composed of watersoluble glass.

15 Claims, 1 Drawing Sheet

BIODEGRADABLE DEVICE

FIELD OF THE INVENTION

The present invention relates to a biodegradable device to aid healing.

DESCRIPTION OF THE RELATED ART

Advances in surgical techniques, particularly micro-surgical techniques, have enabled operations for re-joining or aligning severed nerves and blood vessels to be undertaken. However, to be successful such operations still rely upon the natural healing and regeneration processes of the body. Thus, even where the surgeon has exerted considerable skill in aligning nerve ends, there will be cases where the parts of nerves fail to re-join, or where the healing process is so slow that the effector muscle has atrophied by the time that the motor nerve connection becomes effective.

Healing, for example nerve regeneration, remains an essentially biological process. Even the most advanced micro-surgical techniques for repairing damaged tissue members merely optimise the environment for the natural process. It is now believed that micro-surgery has maximised the mechanical processes for body repair, but a need still exists for enhancing the healing process still further.

Tubes have been used to repair severed nerves, but have enjoyed little success because the non-biodegradable tubes remained after the regenerating nerve had been established and impeded subsequent maturation of the nerve.

GB-A-2,099,702 describes a structural support member for skeletal and tissue members comprised of a biodegradable glass. However, for the healing process to be successful it is essential that the correct chemical environment is created to optimise the regeneration of the damaged body part, whilst protecting that part from the body's own defence system which can be activated against implanted foreign bodies.

In one aspect, the present invention provides a biodegradable device of hollow construction having first and second apertures, each aperture being adapted to receive a cut end of a tissue member which is secured therein by means of a fixant, and wherein at least part of the portion of said device between said apertures contains a substance to facilitate healing of said tissue member.

Generally the device will be tubular. For example the device may be an open-ended tube, the two open ends forming the apertures for receiving the ends of the cut tissue member.

For convenience of manufacture the device may be essentially an open-ended cylinder of uniform internal cross-section. Alternatively, the device may incorporate a reservoir portion, in which reserves of the substance are located. In this embodiment the device may be tubular, but have an internal cross-section of varying diameter, for example of increased diameter in the portion between said apertures. To optimise the healing together of the two cut ends secured in the device, the apertures may be arranged to face each other. However, in certain instances this arrangement may not be essential, and the aperatures need not be aligned.

The device of the present invention may be formed from a biodegradable glass. Such glasses are known to those skilled in the art and the composition of the glass may be adjusted to produce a glass composition that biodegrades over the period required, for example 1 to 6 months, or 1 to 3 months. Desirably the products resulting from degradation of the glass are physiologically compatible.

Additionally, the glass composition may itself be used as a vehicle to deliver biologically active agents in a controlled release manner over the period during which healing occurs. Controlled Release Glasses (CRG) are inorganic polymers, normally based on phosphates of sodium and calcium, which have been converted into a glassy form by melting the constituents at about 1000° C. CRGs dissolve in water completely leaving no solid residue.

The rate of dissolution can be selected by adjustment of the composition and physical form of the CRG and is constant for as long as any of the material remains. The product can be produced in many physical forms; as a powder or granules, fibre or cloth, tubes, or as cast blocks of various shapes.

As stated above, suitable biodegradable glasses are known in the art, but particular mention may be made of the glasses disclosed in WO-A-90/08470 of Giltech Limited. Typically, the glass compositions may comprise:

| | |
|---|---|
| $Na_2O$ | 7–33 mole % |
| $K_2O$ | 0–22 mole % |
| CaO | 0–21 mole % |
| MgO | 0–22 mole % |
| $P_2O_5$ | 46–49 mole % |

Such glass compositions may achieve solution rates of from 0.03 to 3.0 $mgcm^{-2}hr^{-1}$ in de-ionised water at 37° C.

Elements other than sodium and calcium, including most metals as their oxides and a limited number of inorganic anions, can be included in the composition of the glass. These elements, which may be biologically active, can then be delivered at a constant rate into an ambient aqueous medium (for example a physiological fluid) as the CRG dissolves. This has found application in veterinary medicine as a means of delivering such diverse substances as trace elements, anthelmintics and vaccines. Incorporation of a silver source (for example silver orthophosphate) into the $Na_2O$—CaO—$P_2O_5$ systems offers the possibility of producing a CRG capable of releasing silver ions over a highly defined time, into biological systems with safety.

In the course of developments of this type the biocompatibility and absence of toxicity of CRG based on $Na_2O$—(Ca,Mg)O—$P_2O_5$ with and without other constituents have been investigated. In applications differing as widely as use in orthodontics devices [see Savage, Brit. J. of Orthodontics 9:190–193 (1982)], and in controlled supply of Cu, Co and Zn in cattle [see Drake et al, Biochem. Soc. Trans. 13:516–520 (1985)], no ill effects were observed. When CRG pellets were implanted subcutaneously, intramuscularly and intraperitoneally in rats, sheep and cattle, reaction at the implant site was limited to a sterile fibrous encapsulation less well developed than that expected from biocompatible surgical materials [see Allen et al, Vet. Soc. Commun 2:78–75 (1978)]. Other application of CRG in the $Na_2O$—CaO—$P_2O_5$ system have been found as potential bone graft adjuncts/substitutes. No sign of cytotoxicity was observed after soft tissue implantation in sheep [see Burnie et al, Biomaterials 2:244–246 (1981)]. In further experiments with bone no ill effects nor bioincompatibility could be detected [see Burnie et al, "Ceramics in Surgery" Ed Vincenzini, Elseveier Scientific, 1983, pages 169–176; Burnie et al, J. Bone & Joint Surgery 65B(3):364–365 (1983); Duff et al, Strathclyde Bioengineering Seminars, Biomaterials in Artificial Organs, and Paul et al, Macmillan Press, 1984, pages 312–317].

The glass composition may include one or more metal ions which are slowly released from the composition to facilitate healing. Mention may be made of K, Mg, Zn, Al, Se, Si, Fe, Ag, Cu, Mn, Ce and/or Au.

In particular the glass composition may be manufactured to provide a potassium-rich environment, which may be useful in aiding healing of the tissue member, especially nerves.

The substance located in the device will be selected to facilitate healing of the cut tissue member. The viscosity, osmolality and pH of the substance should therefore be chosen to be physiologically compatible with the type of tissue to be healed. The substance may optionally contain one or more physiologically active agents and mention may be made of growth factors (especially growth factors specific for the type of tissue concerned, such as nerve growths factors for nerve re-generation), anti-coagulants, agents to combat infections (for example antibiotics, silver ions etc) and the like. Mention may be made of platelet released and PDGF, Nerve growth factor, Keratinocyte stimulation factors, Insulin-like growth factor, Interleukins, peptides, enzymes and other topical agents, oxygenators and free radical scavengers, enzymes and nutritional agents such as proteins and vitamins. Optionally the surfaces of the glass device may be coated with silicone to reduce thrombogenesis.

Over a number of years a great deal of evidence has emerged from in vitro experiments to suggest that the group of substance known as 'nerve growth factors' or 'nerve cell rescue factors' may enhance the regeneration process which takes place after a nerve is injured and repaired. There are now many such substances awaiting evaluation. Some are thought to act preferentially on either motor or sensory nerves and the potential for their use in chemically manipulating and improving the results of surgical nerve repair is enormous. Despite at least 20 years of study in the laboratory little or no success has been achieved in the method of delivery to this site of injury and also because the tests which are used to quantify nerve repair are insufficiently sensitive to resolve the small (but most useful) benefits which growth factors may bring. For a substance to have maximal effect is must be delivered at the site of regeneration, at an appropriate and maintained concentration and at the time at which its effect on the growing nerve axons will be most effective. To achieve this, delivery must be constant at the site of injury over the growing period and diffusion away from this site must be insufficient for the local concentration to fall below effective values. Lundborg [see G. Lundborg, Nerve Injury and Repair, 1988, Edinburgh Churchill-Livingston] has to a small extent achieved this by wrapping the site in silicon tubes containing growth factors. However there is still an inadequate concentration over time and the permanent tube constricts the growing nerve in its maturation phase. The end result is worse rather than better and no surgeon in human practice would contemplate a second operation to remove a silicon tube.

The biodegradable device of the present invention offers two features which address these issues. First the device can be made to dissolve over a timecourse which would include the period of growth in length when growth factors could be delivered to an isolated environment but dissolution would occur before the non-growth-factor-dependant phase of maturation (growth in diameter). Secondly, growth factors could be delivered into the device through a side hole by means of an osmotic pump. If the outlet silicon rubber tube is glued into the device a watertight system is effected. Using proprietary osmotic pumps, growth factors can be delivered in appropriate constant concentration for four weeks after repair. This encompasses the time for growth factor-dependant regeneration. At the end of this time the device will biodegrade and the pump and its tubing can be removed from its remote subcutaneous site under local anaesthetic in a very small and simple operation. The nerve is thus left unimpeded to mature.

The substance may be any means to facilitate healing, including cellular matrices which encourage and mechanically guide regeneration e.g. of nerve or muscle, and/or humeral substances such as chemical growth factors. By increasing the concentration of the supplied substance at the site of injury and regeneration the latter may be enhanced and its specificity improved.

The fixant may be any means of securing the cut end of the tissue member into an aperture of the device. Desirably the fixant substantially seals the tissue member end into the aperture. Mention may be made of sutures, clips and other mechanical means, but desirably the fixant should be biodegradable. Thus physiologically compatible "glues" may be preferred. One particular example is a fibrin-based tissue glue.

The device itself nay comprise means to secure a tissue member end in an aperture of the device. For example, the internal diameter of the device may decrease in the proximity of the aperture. In one preferred embodiment the device includes internal barbs which grip the tissue member once inserted. Desirably however a physiologically acceptable "glue" is used to seal the aperture after insertion of the tissue member. Thus the glue can be used to protect the damaged ends of the tissue member from the body's defence mechanisms.

The device of the present invention is particularly useful for enhancing the healing of severed nerves, including individual nerve fibres as well as nerve bundles. The device may also be of utility for aiding the healing of tissue members such as tendons, blood vessels (especially capillary blood vessels), muscle fibres and ducts.

The ends of the tissue member may be inserted into the aperture of the device by any suitable means. For example, the aperture may be large enough for the tissue member end to be simply placed therein; the end then being secured by any suitable means, preferably a physiologically acceptable glue. However in certain circumstances it may be desirable for the aperture to be of similar internal diameter to the external diameter of the tissue member. In this instance a suture, threaded through the device is drawn through the tissue member end which can then be pulled through the aperture as required.

In one embodiment the device has a semi-porous or porous region, preferably located between said aperatures. Prior to implantation the device is exposed to physiologically useful agents which may be taken up into the porous or semi-porous region of the device for release after implantation. The agents may facilitate the healing of the tissue member. Thus, the same device could be used to facilitate healing for different types of tissue members, but will be adapted specifically for each depending on the physiologically useful agents taken up into the porous or semi-porous region. Following implantation, said physiologically useful agent(s) can be injected adjacent to the implant, pass through the porous region and onto the tissue member under repair.

In a further embodiment, the device may include an opening to enable introduction of a substance into the device before implantation and/or after implantation. The opening may optionally also be used for exit of the suture pulling the end of the tissue member through the aperature. In one particular embodiment the device of the present invention may be replenished with the substance after implantation. Thus, for example, the device could be connected to a reservoir external to the patient and/or a time-operated pump to automatically replenish the substance in said device.

In a further aspect, the present invention provides a method to facilitate healing of a cut tissue member, said method comprising inserting each end of said tissue member into a separate aperture therefor in the device of the present invention and securing the tissue member ends into said apertures by means of a fixant.

The technique of inserting the tissue member ends, for example nerve ends, into a tube and securing them there with fibrin-based tissue glue is very simple. This technique dispenses with the need for an operating microscope, expensive microsurgical sutures and instruments and the need for a trained microsurgeon. It may thus have considerable implications for current surgical practice and could further extend the repair of nerves to underdeveloped countries where at present nerve injuries may be untreatable.

In a further embodiment the device of the present invention may be used to test the effect of different factors on tissue healing. For example the device may be considered as a model system in which growth factors may be tested to find out whether and to what extent such factors may be helpful in promoting and directing the natural process of regeneration.

In a yet further embodiment the present invention provides a kit to aid healing of a cut tissue member, said kit comprising a device of hollow construction having two apertures adapted to receive the cut ends of a tissue member; said kit further comprising a physiologically acceptable fixant and a substance to aid healing of said tissue member.

The device of the present invention may also be used in vitro to promote growth of a tissue member; the regenerated tissue member may subsequently be used for transplantation, for example to replace a damaged tissue member.

In a further aspect, the present invention provides a method of treating a human or non-human animal body having a cut tissue member, said method comprising inserting the cut ends of said tissue member into separate aperatures of the device according to the invention. Optionally the device may be used in conjunction with an external reservoir of the substance and/or with a time operated pump to deliver the substance to the device.

DETAILED DESCRIPTION OF THE INVENTION

Figure 1:
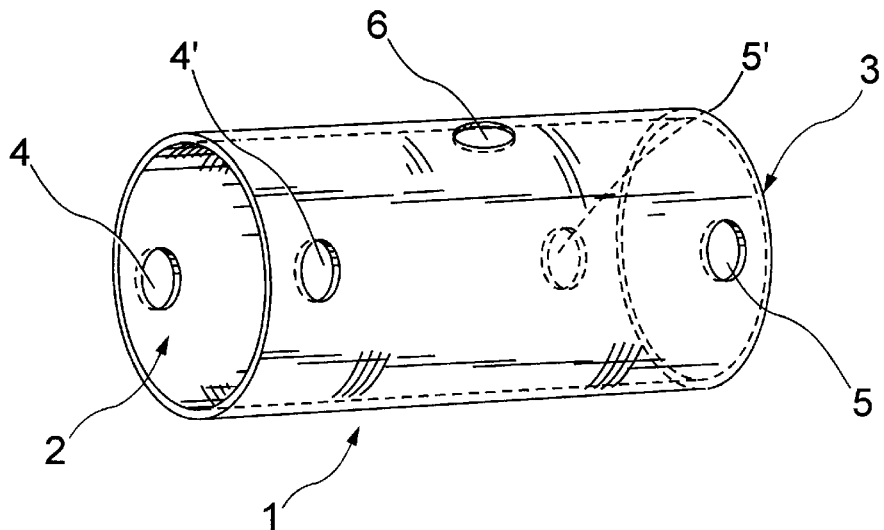
FIG. 1 illustrates a biodegradable glass tube suitable for nerve repair.

FIG. 1 shows a biodegradable glass tube 1 suitable for use in the present invention, especially for nerve repair. Tube 1 consists of a hollow, essentially cylindrical, glass body having aperatures 2, 3 at the ends thereof. Two diametrically opposed suture holes 4,4' are located in tube 1, close to aperature 2. Two similar diametrically opposed suture holes 5,5' are also located in tube 1, close to aperature 3. Approximately mid-way down the length of tube 1 is an injection port 6, which enables access to the interior volume of tube 1, even when tube 1 is in place within a patient.

Figure 2:
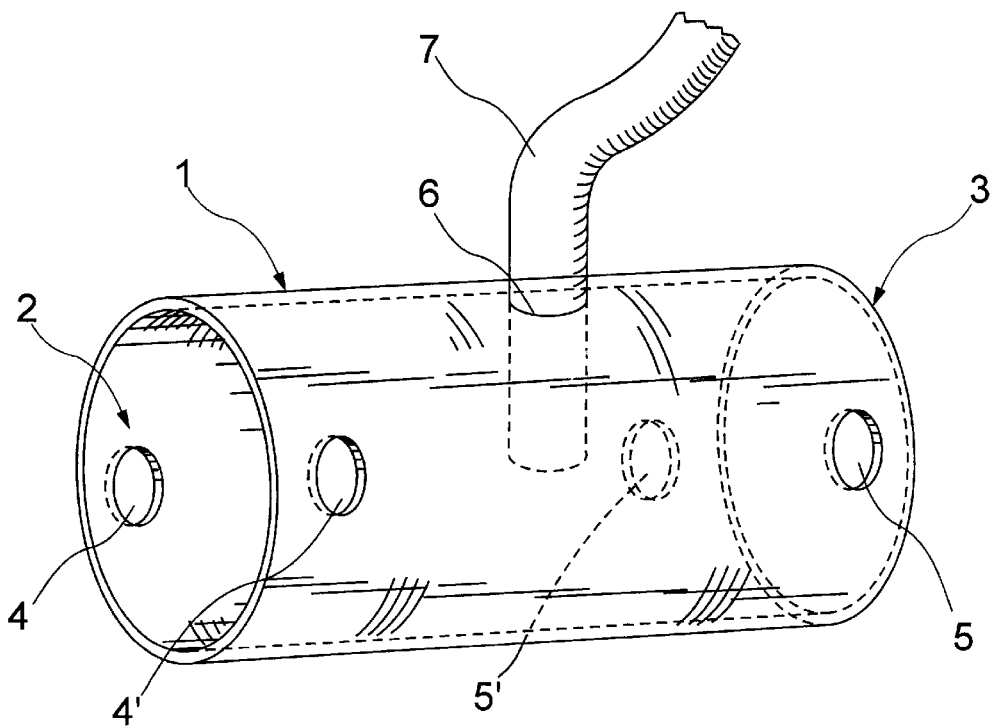
FIG. 2 illustrates the biodegradable glass tube of FIG. 1 having a rubber tubing attached thereto.

FIG. 2 illustrates a similar tube 1 to that shown in FIG. 1, having flexible tubing 7 (for example silicone tubing) passed through injection port 6 into the interior volume of tube 1. Tubing 7 may be connected to a pump or reservoir (not shown) containing a substance or active agent capable of promoting healing of the body part in question. Once sufficient healing has taken place tubing 7 may be simply removed, without disturbing tube 1.

In use, one of the ends of the damaged body part will be inserted into aperature 2 of tube 1, optionally after trimming the end of the body part. A suture will then be passed through a first suture hole 4, through the end of the body part inserted through aperature 2 and out through suture hole 4'. The ends of the suture will then be securely fastened. Optionally a tissue glue may then be used to seal the body part into the aperature 2 of tube 1.

The process described above will then be repeated with the other end of the damaged body part, aperature 3 and suture holes 5,5' of tube 1.

Optionally tubing 7 may be passed through injection port 6 into the interior volume of tube 1 and an appropriate substance fed into the free space within tube 1 to provide an environment suitable for healing the body part. The two ends of the body part will gradually grow down the interior of tube 1 and, on meeting will knit together. Alternatively the substance may be simply injected into the free volume within tube 1 by any suitable means (e.g. syringe).

For very small body parts (e.g. the sciatic nerve of rats, the common peroneal nerve of rabbits or similarly sized body parts of other animals), the length of the glass tube may be 20–26 mm (e.g. 22 mm) with an outer diameter of 4–5 mm. The tube itself may have a thickness of 1–2 mm (e.g. 1.2 mm) and the suture holes and injection ports may each typically have a diameter of 0.5–1 mm (e.g. 0.7 mm).

For slightly larger body parts, a larger dimensioned tube will be required, and the dimensions recited above may be adapted as required. For example in sheep, a tube length of 30 mm having an outer diameter of 8–9 mm and inter diameter of 7 mm, with suture hole and port diameter of 1.2–1.3 mm may be sufficient.

The invention will be further described with reference to the following, non-limiting, examples.

EXAMPLE 1

All procedures were performed on rats and under sterile conditions.

1. The biceps femoris muscle was retracted. Care was taken not to involve the medial femoral circumflex artery which supplies these muscles.

2. The sciatic nerve was cut about 2 cm from the sciatic notch. (Midway down the nerve).

3. A biodegradable glass tube (as illustrated in FIG. 1) was cut to size enabling 2 mm of nerve to extend into the centre of the tube.

The glass of the tube was composed as follows:

|  | Mole % |
| --- | --- |
| $Na_2O$ | 32.0 |
| $CaO$ | 21.0 |
| $P_2O_5$ | 47.0 |

The glass had a solution rate when annealed of 0.4 $mgcm^{-2}hr^{-1}$ in de-ionised water at 37° C. The tube had a physiological life expectancy of approximately 40–50 days.

4. The tube was secured by either suture, clip or glue.

5. The animal was kept for over 60 days before undergoing electrophysiological studies and microscopic analysis under anaesthesia.

6. EMG was taken to measure conduction velocity. The sciatic nerve was exposed as in step 1 and dissected out 2 cm above the graft and 2 cm below. EMG was then taken at each point to determine the speed of conduction:

$$\frac{(EMG \text{ time proximal} - EMG \text{ time distal})}{\text{Distance between points}}$$

The Extensor digitorum longus muscle was chosen for the EMG because the nerve supply is the Deep Peroneal Nerve which is a direct tributary of the Sciatic-Common Peroneal Division.

Results

| Type of Graft | Length (mm) (if removed) | Conduction Velocity (M/s) | Healing time (days) |
|---|---|---|---|
| Tube and Clip | 13 | 4.33 | 46 |
| Tube and Clip | 24 | 25.26 | 67 |
| Tube and Clip | 25 | 31.25 | 114 |
| Tube and Suture | 12.5 | 8.06 | 47 |
| Tube and Suture | 38 | 19.46 | 68 |
| Tube and Suture | 27 | 31.76 | 68 |
| Tube and Suture | 15 | 21.43 | 90 |
| Tube and Suture | 18 | 21.18 | 90 |
| Tube and Suture | 23 | 17.04 | 96 |
| Normal | 18 | 36 | — |

EXAMPLE 2

A further study was conducted to establish:

a) that a biodegradable glass tube (BGT) was compatible with effective nerve repair; and b) that the BGT was not toxic to the regenerating nerve or to the surrounding tissue and that the BGT did not provoke a fibrotic tissue reaction or immune response likely to affect nerve regeneration adversely.

The experiments were performed in rats. The sciatic nerve was divided and a BGT (as used in Example 1) placed over it. With the BGT pushed to one side the nerve stumps were repaired by epineurial suture. The BGT was then placed at the repair site and fixed in place with epineurial sutures and fibrin glue. Electrophysiological and morphometric assessment was carried out at 100 days. It was found that normal nerve regeneration had taken place and that the BGT had completely dissolved. There was no sign of any adverse reaction.

EXAMPLE 3

This experiment was conducted on New Zealand large white rabbits. In each rabbit the common peroneal nerve was divided and repaired in the upper thigh. The tibial nerve was left intact. BGTs were all as described in Example 1 and all of 1.5 cm in length. Each of the methods of repair represented by the contents of the tube are accepted clinical techniques for nerve repair with the exception of the gap which was a control and which would not be expected to be compatible with recovery of nerve function.

1) BGT+1 cm gap in nerve (control)
2) BGT+1 cm freeze-thawed muscle autograft (FTMG)
3) BGT+1 cm nerve autograft
4) BGT+nerve and FTMG short lengths in series to length of 1 cm
5) FTMG without tube (control).

There were 5 rabbits in each group.

Each animal was reviewed 6 months after nerve repair. Under anaesthesia the repair site was re-exposed and the nerve was subjected to a number of electrophysiological tests. Some of these tests have become well established as a means of assessing recovery after nerve repair. Others are new tests which are currently being evaluated in an attempt to find tests which will resolve the small but important improvements in nerve regeneration which may be expected where nerve growth factors are used. In all cases the opposite limb was used as a control.

After electrophysiological assessment, the segments of repaired and control nerve were excised and processed for microscopic examination. Computerized morphometric assessment was used to measure indices of nerve regeneration such as axon and fibre diameter and G-ratio.

In group 1 above it was surprising to find that regeneration had taken place albeit to a limited extent. It seems likely that isolating the regenerating nerve within the tube may have improved its chances of crossing the gap. This result speaks well for the fact that the tube does not impede nerve regeneration.

In groups 2, 3 and 4 all of the indices of recovery showed comparability with the best results obtained by conventional means. This means that as a supporting medium for either direct repair or repair using short neural and FTMG grafts the BGT system performs as well as anything else currently available.

Group 2 demonstrated the best results, with all groups 1, 2 and 3 giving successful regeneration of the peripheral nerve. There were no signs of neuroma in any of the groups and the BGT was completely dissolved after the 6 month test period.

We claim:

1. A biodegradable device of hollow construction formed at least in part from biodegradable glass, having first and second apertures, each aperture being adapted to receive a cut end of a tissue member which is secured therein by means of a fixant, wherein at least part of the portion of said device between said apertures contains a substance to facilitate healing of said tissue member, and wherein means to deliver said substance at an appropriate concentration are provided.

2. A device as claimed in claim 1 being an open-ended tube, the two ends of the tube forming the aperatures for receiving the ends of the cut tissue member.

3. A device as claimed in claim 1 having a reservoir portion to hold reserves of said substance.

4. A device as claimed in claim 1 wherein said glass is a controlled release glass.

5. A device as claimed in claim 4 wherein said glass releases silver ions in a controlled release manner. and mixtures thereof.

6. A device as claimed in claim 1 wherein said substance is selected from growth factors, anti-coagulants agents to combat infection, platelet releasate, interleukins, peptides (including enzymes), nutritional agents, and mixtures thereof.

7. A device as claimed in claim 6 wherein said substance includes nerve growth factor.

8. A device as claimed in claim 1 wherein a fixant is used to substantially seal the cut end of the tissue member to an aperature of said device.

9. A device as claimed in claim 9 wherein said fixant is a fibrin-based tissue glue.

10. A device as claimed in claim 1 having internal barbs to grip the inserted tissue member.

11. A device as claimed in claim 1 having a semi-porous or porous region located between said aperatures.

12. A device as claimed in claim 1 in combination with an external reservoir of said substance and/or a time-operated pump to deliver said substance to said device.

13. A kit to aid healing of a cut tissue member, said kit comprising a device of hollow construction having two apertures adapted to receive the cut ends of a tissue member; said kit further comprising a physiologically acceptable fixant and a substance to aid healing of said tissue member.

14. A method of treating a human or non-human animal body having a cut tissue member, said method comprising inserting the cut ends of said tissue member into separate aperatures of a device as claimed in claim 1.

15. A method as claimed in claim 14 wherein said device is used in conjunction with an external reservoir of said substance and/or a pump to deliver said substance to the device.

* * * * *

UNITED STATES PATENT AND TRADEMARK OFFICE
CERTIFICATE OF CORRECTION

PATENT NO. : 5,972,371
DATED : October 26, 1999
INVENTOR(S) : Gilchrist et al.

It is certified that error appears in the above-identified patent and that said Letters Patent is hereby corrected as shown below:

In the specification, column 1, line 60, delete "aperatures" and insert --apertures--.

In the specification, column 4, line 50, delete "aperatures" and insert --apertures--.

In the specification, column 5, line 61, delete "aperature" and insert --aperture--.

In the specification, column 5, line 62, delete "aperature" and insert --aperture--.

In the specification, column 6, line 11, delete "aperature" and insert --aperture--.

In the specification, column 6, line 16, delete "aperature" and insert --aperture--.

In claim 2, column 8, line 47, delete "aperatures" and insert --apertures--.

In claim 5, column 8, line 54, after "manner.", please delete "and mixtures thereof."

UNITED STATES PATENT AND TRADEMARK OFFICE
CERTIFICATE OF CORRECTION

PATENT NO. : 5,972,371
DATED : October 26, 1999
INVENTOR(S) : Gilchrist et al.
BIODEGRADABLE DEVICE It is certified that error appears in the above-identified patent and that said Letters Patent is hereby corrected as shown below:

In claim 8, column 8, line 65, delete "aperature" and insert --aperture--.

In claim 9, column 8, line 66, delete "claim 9" and insert --claim 8--.

Signed and Sealed this

Eleventh Day of July, 2000

Attest:

Q. TODD DICKINSON

Attesting Officer

Director of Patents and Trademarks